United States Patent
Gonzalez et al.

(10) Patent No.: US 7,118,760 B2
(45) Date of Patent: Oct. 10, 2006

(54) ESTERS OF ARYL BENZIMIDAZOLE SULFONIC ACIDS AND SUNSCREEN COMPOSITIONS CONTAINING SAME

(75) Inventors: Anthony D. Gonzalez, Oak Ridge, NJ (US); Andrew H. Pechko, Ridgewood, NJ (US); Glen T. Anderson, Pleasantville, NY (US); Robert E. Kalafsky, Ogdensburg, NJ (US); Michael V. Lowenborg, Bethpage, NY (US)

(73) Assignee: Avon Products, Inc., New York, NY (US)

( * ) Notice: Subject to any disclaimer, the term of this patent is extended or adjusted under 35 U.S.C. 154(b) by 475 days.

(21) Appl. No.: 10/744,875

(22) Filed: Dec. 23, 2003

(65) Prior Publication Data

US 2005/0136014 A1 Jun. 23, 2005

(51) Int. Cl.
*A61K 8/19* (2006.01)
*A61K 8/02* (2006.01)
*A01N 25/04* (2006.01)
*C07D 235/04* (2006.01)

(52) U.S. Cl. .................. 424/405; 424/59; 424/401; 519/919; 548/304.4; 548/304.7; 548/305.4

(58) Field of Classification Search ............... 424/401, 424/59, 405; 548/304.4, 304.7, 305.4; 514/919
See application file for complete search history.

(56) References Cited

U.S. PATENT DOCUMENTS

| | | | |
|---|---|---|---|
| 5,718,906 A * | 2/1998 | Martin et al. ............... | 424/401 |
| 6,238,657 B1 | 5/2001 | Lin et al. .................. | 424/70.12 |
| 6,262,170 B1 | 7/2001 | Kilgour et al. ............. | 524/731 |
| 6,517,816 B1 | 2/2003 | Gonzalez et al. ............ | 424/59 |

OTHER PUBLICATIONS

International Search Report dated Mar. 20, 2006.

* cited by examiner

*Primary Examiner*—Kamal A. Saeed
*Assistant Examiner*—Ebenezer Sackey
(74) *Attorney, Agent, or Firm*—Ohlandt, Greeley, Ruggiero & Perle, L.L.P.

(57) ABSTRACT

The present invention provides novel aryl benzimidazole sulfonic acid esters and cosmetic compositions that employ the novel aryl benzimidazole sulfonic acid esters as sunscreens. The cosmetic compositions can be water, organic solvent or emulsion based. Also provided are methods of using the compositions to protect skin from exposure to the sun, and optionally, repel insects.

29 Claims, No Drawings

ESTERS OF ARYL BENZIMIDAZOLE SULFONIC ACIDS AND SUNSCREEN COMPOSITIONS CONTAINING SAME

BACKGROUND OF THE INVENTION

1. Field of the Invention

The present invention relates to esters of aryl benzimidazole sulfonic acids and their use as sunscreens in cosmetic compositions. More particularly, the present invention relates to compositions having esters of phenyl benzimidazole sulfonic acids with $C_{16}$ to $C_{50}$ alcohols and/or siloxane derivatives.

2. Description of the Related Art

Increased stability and increased sun protection benefits and reduced level of sunscreen required for effective sun protection and other performance characteristics are desirable attributes in sun care, skin care, hair care and personal care and cosmetic products, compositions and preparations.

For example, water resistance is a much-desired quality amongst consumers of color cosmetics, lipsticks, eyelash mascara, insect repellents, sunscreen preparations and sunscreen and insect repellent combinations, jelly fish repellent, poison ivy, poison oak, and poison sumac protective compositions. Additionally, shine and gloss are much desired attributes in nail color and hair care preparations. Surface smoothening can be important in a shampoo, hair conditioner, styling mousse and other hair treatment preparation, and can provide superior wet and dry hair combing.

Thus, there is a need in consumer products and cosmetic industry for formulations that can enhance the effectiveness of the various active ingredients contained therein and can deliver multiple benefits, such as, increased water resistance, increased stability, improved permanence, and increased performance characteristics, such as, increased sun protection benefits and reduced level of sunscreen required for effective sun protection.

Aryl benzimidazole sulfonic acid sunscreens known in the art are insoluble organic acids that must be converted to the salt form to make them suitable for use in cosmetic formulation. The use of salts imposes great constraints on the ability of the cosmetic formulators to produce waterproof sunscreens with acceptable aesthetics. For example, the effectiveness of carbomers, as well as some waterproofing polymers such as Diglycol/CHDM/Isophthalates/SIP Copolymer, is diminished in the presence of various levels of salt.

In contrast, the present invention provides novel sulfonate esters that are soluble in oil, which are easy to use raw material for cosmetic compositions and provide greater substantivity.

In applications that involve skin contact, the large molecular configuration of the present invention allows the chromophore to remain on the surface of the skin where it is more effective due to its reduced solubility in water.

Known aryl benzimidazole sulfonic acids and their water-soluble salts are insoluble in organic solvent systems. As a result, they must be incorporated into the water phase of a sunscreen composition where they have the potential to be washed off from the skin upon perspiration or exposure to water.

Further, sunscreen esters commonly used employ lower carbon organic groups, such as, $C_8$ groups. Sunscreens with lower carbon organic groups do not exhibit good water resistance or sweat resistance.

The present invention addresses the problems of permanence associated with sunscreen agents, while maintaining the high extinction coefficients of the parent molecule.

In addition, the conjugated structure of the present invention allows for resonance delocalization to occur, while keeping the UV absorbance in the desired range for sun protection.

U.S. Pat. No. 6,262,170 describes a composition having an insoluble swollen gel network of a silicone elastomer of MDTQ structural type.

U.S. Pat. No. 6,238,657 also uses elastomers to form oil in silicone emulsions.

U.S. Pat. No. 6,517,816 describes a metastable sunscreen water-in-oil emulsion composition having an inner discontinuous phase and an outer continuous phase. There is no mention of any composition that has aryl benzimidazole sulfonic acid esters.

The present invention is applicable to a variety of personal care products including, but not limited to skin care, hair care, personal care, and color cosmetics.

SUMMARY OF THE INVENTION

It is an object of the present invention to provide novel esters of aryl benzimidazole sulfonic acids.

It is another object of the present invention to provide cosmetic compositions that employ the novel esters of the present invention as sunscreens.

It is still another objective of the present invention to produce multifunctional sunscreens that are oil soluble and therefore are easy to use.

It is yet another object of this invention to provide sunscreen compositions having the novel sunscreens of the present invention as sunscreen actives.

It is yet another object of the present invention to provide ease of formulation of waterproof, water resistant, sweat proof and sweat resistant sunscreens.

It is a further object of the present invention to provide cosmetic compositions having an insect repellent in addition to the novel sunscreens of the present invention.

It is still a further object of the present invention to provide a cosmetic product, such as, sun care, skin care, and personal care.

The present invention provides such sunscreens, cosmetic compositions, methods, and products that employ the novel sunscreens of the present invention.

Accordingly, the present invention provides a sunscreen represented by the formula:

(a)

$$R-O-\underset{\underset{O}{\overset{\displaystyle O}{\|}}}{S}\text{-benzimidazole-aryl with substituents } R^1, R^2, R^3, R^4, R^5, R^6, R^7, R^8, R^9$$

-continued (b)
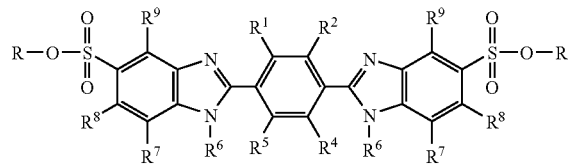

(c)
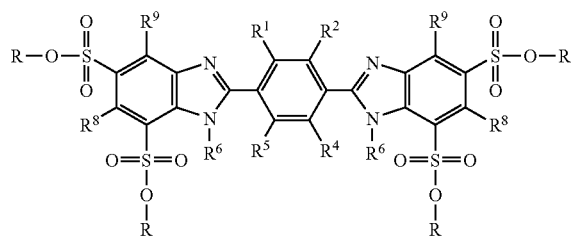

or (d) any mixtures thereof;

wherein each R is independently a linear, branched or cyclic $C_{16}$ to $C_{50}$ alkyl; a linear, branched or cyclic $C_{16}$ to $C_{50}$ alkyl interrupted, substituted, or interrupted and substituted by one or more groups each of which can be aryl, heteroaryl, O, S, SO, $SO_2$, CO, COO, halogen, cyano, ester, ether, keto, hydroxy, alkoxy, aryloxy, amino, amido, —[O(Si($R^{10})_2]_n$—, or $R^{10}[Si(R^{10})_2]_n$—; a $C_6$ to $C_{24}$ aryl; a $C_6$ to $C_{24}$ aryl substituted by one or more groups each of which can independently be aryl, heteroaryl, O, S, SO, $SO_2$, CO, COO, halogen, cyano, ester, ether, keto, hydroxy, alkoxy, aryloxy, amino, amido, or $R^{10}[Si(R^{10})_2]_n$—; a $C_4$ to $C_{24}$ heteroaryl; a $C_4$ to $C_{24}$ heteroaryl substituted by one or more groups each of which can independently be halogen, cyano, ester, ether, keto, hydroxy, alkoxy, aryloxy, amino, amido, or $R^{10}[Si(R^{10})_2]_n$—; $R^{10}[Si(R^{10})_2]_n$—; and $R^{11}$ which is a silicone residue derived from a silicone represented by the formula $R^{11}OH$ having a weight average molecular weight up to about 30,000;

each $R^1$, $R^2$, $R^3$, $R^4$, $R^5$, $R^7$, $R^8$, and $R^9$ can independently be hydrogen, halogen, cyano, ester, ether, keto, hydroxy, alkoxy, aryloxy, amino, amido, a linear, branched or cyclic alkyl of 1–12 carbon atoms, a substituted linear, branched or cyclic alkyl of 1–12 carbon atoms, an aryl of 5–12 carbon atoms, a substituted aryl of 5–12 carbon atoms, a heteroaryl of 4–12 carbon atoms, and a substituted heteroaryl of 4–12 carbon atoms; wherein each substituent in the substituted alkyl, substituted aryl and substituted heteroaryl groups is independently aryl, heteroaryl, halogen, cyano, ester, ether, keto, hydroxy, alkoxy, aryloxy, amino, or amido;

each $R^6$ is independently hydrogen, an alkyl of 1–12 carbon atoms, or a substituted alkyl of 1–12 carbon atoms;

each $R^{10}$ is independently alkyl, alkoxy, aryl or aryloxy; and n is from 1 to about 500.

The present invention further provides a cosmetic composition having sunscreens according to the present invention and a cosmetically acceptable vehicle.

Due to the high extinction coefficient of the esters of aryl benzimidazole sulfonic acids, a high SPF can be obtained with low amounts of the present sunscreens.

The advantages are ease of formulation of sulfonic acid ester based sunscreens. Also, aryl benzimidazole sulfonic acid esters with $C_{16}$–$C_{50}$ branched or linear chain alcohols and/or silicones exhibit increased substantivity, waterproofing, water resistance, sweat proofing, sweat resistance, rub-off resistance, and improved solubility in the oil phase of cosmetic compositions. In addition, the present invention allows the use of benzimidazole sulfonates in systems with salt intolerant natural and synthetic clays, gums, and polymers.

The aryl benzimidazole sulfonic acid esters have utility in cosmetic and personal care preparations.

These and other objects and advantages of the present invention are achieved by the use of the sunscreens according to the present invention to provide effective sun protection an-M SUSvd good waterproof performance in cosmetic and personal care products applications.

DETAILED DESCRIPTION OF THE INVENTION

The present invention provides the following sunscreens represented by formula (a) through (c):

(a)
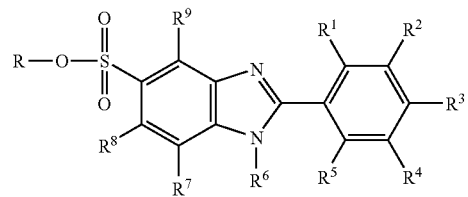

(b)
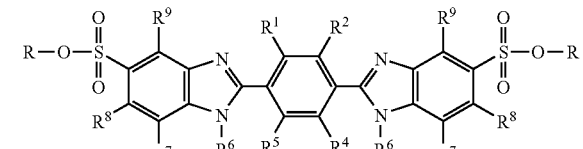

(c)
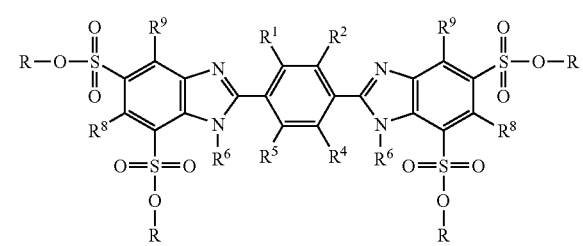

or (d) any mixtures thereof;

wherein each R is independently a linear, branched or cyclic $C_{16}$ to $C_{50}$ alkyl; a linear, branched or cyclic $C_{16}$ to $C_{50}$ alkyl interrupted, substituted, or interrupted and substituted by one or more groups each of which can be aryl, heteroaryl, O, S, SO, $SO_2$, CO, COO, halogen, cyano, ester, ether, keto, hydroxy, alkoxy, aryloxy, amino, amido, —[O(Si($R^{10})_2]_n$—, or $R^{10}[Si(R^{10})_2]_n$—; a $C_6$ to $C_{24}$ aryl; a $C_6$ to $C_{24}$ aryl substituted by one or more groups each of which can independently be aryl, heteroaryl, O, S, SO, $SO_2$, CO, COO, halogen, cyano, ester, ether, keto, hydroxy, alkoxy, aryloxy, amino, amido, or $R^{10}[Si(R^{10})_2]_n$—; a $C_4$ to $C_{24}$ heteroaryl; a $C_4$ to $C_{24}$ heteroaryl substituted by one or more groups each of which can independently be halogen, cyano, ester, ether, keto, hydroxy, alkoxy, aryloxy, amino, amido, or $R^{10}[Si(R^{10})_2]_n$—; $R^{10}[Si(R^{10})_2]_n$—; and $R^{11}$ which is a silicone residue derived from a silicone represented by the formula $R^{11}OH$ having a molecular weight up to about 30,000;

each $R^1$, $R^2$, $R^3$, $R^4$, $R^5$, $R^7$, $R^8$ and $R^9$ can independently be hydrogen, halogen, cyano, ester, ether, keto, hydroxy, alkoxy, aryloxy, amino, amido, a linear, branched or cyclic alkyl of 1–12 carbon atoms, a substituted linear, branched or cyclic alkyl of 1–12 carbon atoms, an aryl of 5–12 carbon atoms, a substituted aryl of 5–12 carbon atoms, a heteroaryl of 4–12 carbon atoms, a substituted heteroaryl of 4–12 carbon atoms, wherein each substituent in the substituted alkyl, substituted aryl and substituted heteroaryl groups is independently aryl, heteroaryl, halogen, cyano, ester, ether, keto, hydroxy, alkoxy, aryloxy, amino, or amido;

each $R^6$ is independently hydrogen, an alkyl of 1–12 carbon atoms, or a substituted alkyl of 1–12 carbon atoms;

each $R^{10}$ is independently alkyl, alkoxy, aryl or aryloxy; and n is from 1 to about 500.

The $R^{11}OH$ can be a substituted or unsubstituted siloxane and a substituted or unsubstituted organosiloxane.

In a preferred embodiment, each R can independently be one or more of linear, branched or cyclic $C_{16}$ to $C_{40}$ alkyls, $C_{17}$ to $C_{50}$ alkyls, $C_{17}$ to $C_{40}$ alkyls, $C_{18}$ to $C_{50}$ alkyls, $C_{18}$ to $C_{40}$ alkyls, $C_{19}$ to $C_{50}$ alkyls, $C_{19}$ to $C_{40}$ alkyls, $C_{20}$ to $C_{50}$ alkyls, $C_{20}$ to $C_{40}$ alkyls, $C_{21}$ to $C_{50}$ alkyls, $C_{21}$ to $C_{40}$ alkyls, $C_{22}$ to $C_{50}$ alkyls or $C_{22}$ to $C_{40}$ alkyls. Also, any combinations of any alkyls within the $C_{16}$ to $C_{50}$ alkyl range are also contemplated by the present invention.

In another preferred embodiment, R can be a linear $C_{16}$ to $C_{50}$ alkyl or a linear $C_{16}$ to $C_{50}$ alkyl interrupted or substituted by one or more groups each of which can independently be O, S, $SO_2$, COO, halogen, ester, alkoxy, hydroxy, $-[O(Si(R^{10})_2]_n-$, or $R^{10}[Si(R^{10})_2]_n-$, and $R^{10}$ is alkoxy.

In still other preferred embodiments, $R^{11}$ is $R^{10}[Si(R^{10})_2]_n-$, the molecular weight of the $R^{11}OH$ is about 100 to about 5,000, each $R^1$, $R^2$, $R^3$, $R^4$, $R^5$, $R^7$, $R^8$ and $R^9$ is hydrogen, each $R^6$ can independently be hydrogen or an alkyl, and n is from 1 to about 100.

Examples of the preferred aryl benzimidazole sulfonic acid esters include phenyl benzimidazole sulfonic acid esters with organic alcohols or silicones represented by the following formulas:

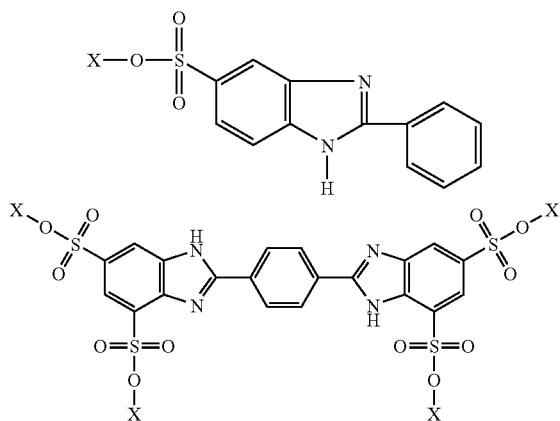

wherein each X can independently be a $C_{16}$ to $C_{50}$ branched or linear, substituted or unsubstituted alkyl group or siloxane or organosiloxane group. Preferably, each X is independently a linear, branched or cyclic $C_{17}$ to $C_{50}$ alkyls, $C_{18}$ to $C_{50}$ alkyls, $C_{19}$ to $C_{50}$ alkyls, $C_{20}$ to $C_{50}$ alkyls, $C_{21}$ to $C_{50}$ alkyls, $C_{22}$ to $C_{50}$ alkyls, $C_{17}$ to $C_{40}$ alkyls, $C_{18}$ to $C_{40}$ alkyls, $C_{19}$ to $C_{40}$ alkyls, $C_{20}$ to $C_{40}$ alkyls, $C_{21}$ to $C_{40}$ alkyls, or $C_{22}$ to $C_{40}$ alkyls.

The silicone residues in the sulfonate ester sunscreens of the present invention, such as silicone residue represented by the formula $R^{11}$ is $R^{10}[Si(R^{10})_2]_n-$, are derived from the corresponding silicone alcohols, i.e., hydroxy group containing silicones, including silicone alcohols, such as, hydroxy substituted and hydroxy terminated silicones.

Examples of hydroxyl functional silicones include Dimethiconol, which is sold under the trade name of Dow Corning 2-9023, Silicone Fluid NM 201-50.000, Unisil SF-R, silanol, methylsilanol, other organomodified silanols, such as, Dow Corning 1248 fluid, and a polydimethylsiloxane polymer having a terminal silanol functionality, such as, for example, 2-1273 fluid from Dow Corning.

Aryl benzimidazole sulfonic acid esters with hydroxy functional sunscreens, such as, alcohols, can be prepared by esterification of an aryl benzimidazole sulfonyl halide, such as, an aryl benzimidazole sulfonyl chloride, with the hydroxyfunctional compound, preferably in the presence of a base, preferably under anhydrous conditions, that are generally used for such reactions. Modified Schotten-Baumann reaction conditions may also be used provided anhydrous reaction conditions are maintained.

Preferred bases are those that are capable of removing the hydrogen halide formed during the esterification reaction without reacting with the sulfonyl halides. Such bases include hindered amines, such as, 2,2,6,6-tetramethylpiperidenes, diazabicyclooctanes, such as, DABCO, diazabicyclononanes, diazabicyclodecanes, trioctylamine, tridecylamine, tridodecylamine, pentamethyl guanidine, lutidine, proton sponges, such as, 1,10-bis(dimethylamino)naphthalene, basic alumina, basic silica gel, and any combinations thereof.

The aryl benzimidazole sulfonyl halides can be obtained from the corresponding sulfonic acids by reaction with a halogenating agent, such as, $PCl_3$, $PCl_5$, $POCl_3$, and $PCl_3/Cl_2$ mixture.

The present invention also provides a cosmetic composition that has a cosmetically acceptable vehicle and an effective amount of one or more of the novel sunscreens, i.e., "sunscreen actives," according to the present invention.

The cosmetic composition can be organic solvent based, water based or it can be an emulsion. Such organic solvent, water, or emulsion-based compositions are known in the art and therefore, are not discussed further herein. However, neither the oil in silicone emulsions nor oil in silicone/water in silicone emulsions have been known or described in the prior art. Such emulsions are described in greater detail herein below.

The cosmetic compositions have a cosmetically acceptable vehicle and contain an effective amount of one or more of the novel sunscreens according to the present invention.

The cosmetic composition can further have one or more "actives," such as, insect repellents, jelly fish repellent, poison ivy, oak or sumac protective agents, anesthetics, anti-allergenics, antifungals, antimicrobials, anti-inflammatory agents, antiseptics, exfollients, pharmaceuticals, film formers, additional sunscreens, or any combinations thereof.

Preferably, the active ingredient is a sunscreen active, an insect repellent, or any mixtures thereof.

In the case where the active ingredient is a mixture of a sunscreen and an insect repellent, the mixture of the sunscreen and insect repellent is up to about 70 wt % of the total weight of the emulsion.

The preferred insect repellents include oil of citronella, DEET, and IR 3535, which has the following chemical formula:

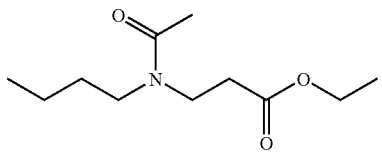

ethyl 3-(N-butylacetamino)propionate

Ethyl 3-(N-butylacetamino)propionate is sold under the commercial name Merck IR 3535 and is available from Merck Corporation.

The effective amount of the insect repellent active for providing insect protection benefit is about 1 wt % to about 50 wt % of the total weight of the emulsion. More preferably, the effective amount of the insect repellent active is about 2.5 wt % to about 35 wt % of the total weight of the emulsion. Most preferably, the effective amount of the insect repellent active is about 5 wt % to about 15 wt % of the total weight of the emulsion.

Preferably, the additional sunscreen can be, but is not limited to, one or more of the following:

dibenzoylmethane, oxybenzone, sulisobenzone, dioxybenzone, menthyl anthranilate, para aminobenzoic acid (PABA) ester, benzophone-3, butyldibenzoylmethane (Parsol 1789), dimethyl cinnamate, octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, 3-benzylidene camphor, benzylidene camphor sulfonic acid ester, octyl triazone, phenyl benzimidazole sulfonic acid ester, terephthalydiene dicamphor sulfonic acid ester, di-t-butyl hydroxybenzylidene camphor, ethyl PABA, butyl-methoxy dibenzoylmethane (avobenzone), terephthalydiene methylene bis-benzotriazoyltetramethylbutyl-phenol, diethylhexyl-2,6-naphthalate, bis-ethylhexyloxyphenol methoxyphenol triazine, hydroxy methylphenyl benzotriazole, methylene bis-benzotriazoyltetramethylbutylphenol, bis-ethylhexyloxyphenol methoxyphenol triazine, hydroxybenzophenone, a benzotriazole, a dibenzoyl methane, an oxanilide, a hydroxy cinnamate, oil dispersible titanium dioxide, oil dispersible zinc oxide, a silicone-anchored sunscreen, para aminobenzoic acid (PABA), salicylic acid, TEA salicylate, benzylidene camphor sulfonic acid, phenyl benzimidazole sulfonic acid, terephthalydiene dicamphor sulfonic acid, hydroxy cinnamic acid, any derivatives thereof, or any combinations thereof.

Examples of water-soluble sunscreens include, but are not limited to, para aminobenzoic acid (PABA), salicylic acid, TEA salicylate, benzylidene camphor sulfonic acid, phenyl benzimidazole sulfonic acid, terephthalydiene dicamphor sulfonic acid, hydroxy cinnamic acid, any derivatives thereof, and any combinations thereof.

The effective amount of the novel sunscreen for providing sun protection benefit is about 0.01 wt % to about 50 wt %, preferably about 0.5 wt % to about 40 wt %, more preferably about 1 wt % to about 25 wt %, most preferably from about 1 wt % to about 20 wt % of the total weight of the composition. Preferably, the novel sunscreen is present up to about 50 wt % based on the total weight of the composition. More preferably, the sunscreen is at about 1.0 wt % to about 40 wt % based on the total weight of the composition. Most preferably, the sunscreen is present at about 10 wt % to about 35 wt % based on the total weight of the composition.

When the novel sunscreen active of the present invention is used in combination with other sunscreen actives, the total sunscreen in the composition is generally up to about 50 wt %, with the amount of the novel sunscreen of this invention preferably about 0.5 wt % to about 40 wt %, more preferably about 1 wt % to about 25 wt %, and most preferably about 1 wt % to about 20 wt % of the total weight of the composition.

The cosmetic composition exhibits an SPF about 2 to about 100. Preferably, composition exhibits an SPF about 15 to about 75. More preferably, the composition exhibits an SPF about 25 to about 65. Most preferably, the composition exhibits an SPF of about 30 to about 50.

The present compositions typically have a vehicle. The vehicle should be a cosmetically acceptable or suitable vehicle. In the context of the present invention, the term "cosmetically acceptable vehicle" or "suitable vehicle" refer to any vehicle for a drug, a cosmetic or a medicament that is suitable for use in direct, safe contact with human tissues.

The vehicle of the cosmetic composition is preferably suitable for use in applications that require direct contact with human tissue. The tissue is preferably skin. The vehicle can be a solid, a fluid, emulsion, balm, an aerosol or a pump spray.

The solid vehicle is preferably a patch, a tape, or a powder. The fluid vehicle is preferably a liquid, a lotion, and a gel. The cosmetic composition is preferably in a form, such as, shampoo, hair conditioner, styling mousse, hair treatment preparation, hair coloring product, semi-perm product, oxidation dye, body wash, bar soap, liquid soap, skin care preparation, lipstick, mascara, color cosmetic, nail care preparation, cream, foam, gel, lotion, solution, emulsion, pomade, mousse, balm, stick, pump spray, aerosol spray, or any combinations thereof.

The preferred product forms include solution, cream, lotion, pomade, stick, gel, pump spray, and aerosol spray.

The sunscreen can be used as the oil phase, without any additional oil being present in the emulsion.

The sunscreens according to the present invention are generally hydrophobic. Other preferred hydrophobic ingredients that can be used in the compositions of the present invention include additional sunscreens, insect repellents, jelly fish repellents, poison ivy protective agents, poison oak protective agents, poison sumac protective agents and any combinations thereof.

Other suitable additives include:

antioxidants, such as, rosemary extract, tocopherol, a derivative of tocopherol including a tocotriene, carotene, a carotenoid, a phenolic antioxidant including a phenolic acid, a bioflavonoid, a plant extract, curcumin, tetrahydrocurcumin, camphorol, quercetine, epigenine, and any mixtures thereof. The preferred antioxidants are tocopherols and bioflavonoid that have demonstrated antioxidant activity, including ginkgo biloba, pyconogyl pycoogeonyl, pycyogenol, genistein, and daidzein;

keratolytic agents, such as, salicylic acid, resorcinol, peroxide of an organic acid, and any mixtures thereof;

anti-inflammatory agents, such as, steroidal and non-steroidal anti-inflammatory agents and plant extracts that have demonstrated anti-inflammatory activity;

vitamins, such as, Vitamin K, retinol (vitamin A), tocopherol, and any mixtures thereof;

emollients, such as, cetearyl octanoate, octyl palmitate, butylene glycol, propylene glycol, glycerine, glyceryl monostearate, petrolatum, caprylic trigylceride, capric trigylceride, shae butter, and silicone oil;

humectants, such as, glycerin, propylene glycol, butylene glycol, hyaluronic acid, one or more derivatives of hyaluronic acid, and any mixtures thereof;

skin penetration enhancers, such as, ozone, SEPA, butylene glycol, cis-isomer of an unsaturated fatty acid, and any mixtures thereof;

emulsifiers, such as, glyceryl stearate, cetearyl alcohol, cetyl alcohol and PEG-40 stearate;

thickening agents, such as, xanthan gum, carbomer, clay and hydroxyethyl cellulose;

film formers, such as, timethyl siloxysilicate, nitrocellulose, cellulose acetate butyrate, alkyd resins, polyester resins, acrylic resins, low molecular weight polyurethane resins, polyamide resins, vinyl resins, arylsulfonamide aldehyde resins, and arylsulfonamide epoxy resins;

retinoids, such as, retinol, one or more esters of retinol, retinoic acid, one or more esters of retinoic acid, a compound that can mimic retinol, and any mixtures thereof;

preservatives, such as, an alkyl paraben, an alcohol, imidazolidinyl urea, and any mixtures thereof;

colorants, such as, synthetic and natural colorants;

chelating agents, such as, disodium EDTA; and pH adjusters, such as, an acid, a base, or a buffer, to adjust and maintain the pH to about 6.5 to about 7.5.

Other additives include one or more of barium sulfate, silica, nylon polymethylmethacrylates, fibers, plastics, polyethylenes, polypropylenes, PET, PVC, polyesters, proteins, colorants, pigments, including photo-chromic and thermo-chromic colorants and pigments, and other appropriate materials.

The present invention provides a method of protecting skin from exposure to the sun. The method includes the step of applying topically onto the skin an effective amount of a composition having a sunscreen according to the present invention.

The present invention further provides a method of repelling insects from skin. The method includes the step of applying topically onto the skin an effective amount of a composition having an insect repellent according to the present invention.

The present invention still further provides a method of simultaneously protecting skin from exposure to the sun and repelling insects from the skin. This method includes the step of applying topically onto the skin an effective amount of a composition having both a sunscreen and an insect repellent according to the present invention.

The Examples that follow are illustrative of the present invention. They should not be construed as being limiting in any manner.

EXAMPLE 1

| Water | QS to 100% |
| --- | --- |
| Carbomer | 0.75% |
| Preservative | QS |
| Triethanoloamine | to pH 6.5 |
| Octinoxate | 5% |
| Octisalate | 2% |
| Avobenzone | 1% |
| PBSA Ester (1)[a] | 1% |
| C12–15 Alkyl Benzoate | 5% |
| PEG 100 Stearate | 0.8% |

[a]PBSA Ester (1) is phenyl benzimidazole sulfonic acid ester with Dimethiconol, a sulfonate ester according to the present invention

EXAMPLE 2

| Ethanol | QS to 100% |
| --- | --- |
| Oxybenzone | 4% |
| Octocrylene | 10% |
| Homosalate | 8% |
| PBSA Ester (2)[b] | 10% |

[b]PBSA Ester (2) is phenyl benzimidazole sulfonic acid ester with a C-18 alcohol, a sulfonate ester according to the present invention.

It should be understood that the foregoing description is only illustrative of the present invention. Various alternatives and modifications can be devised by those skilled in the art without departing from the present invention. Accordingly, the present invention is intended to embrace all such alternatives, modifications and variations that fall within the scope of the appended claims.

What is claimed is:

1. A sunscreen selected from the group consisting of compounds represented by the formula:

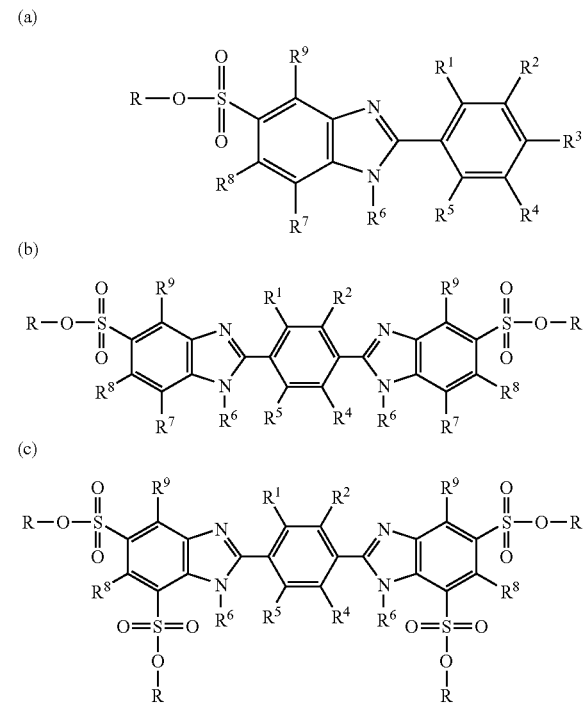

and
(d) any mixtures thereof;
wherein each R is independently selected from the group consisting of a linear, branched or cyclic $C_{16}$ to $C_{50}$ alkyl; a linear, branched or cyclic $C_{16}$ to $C_{50}$ alkyl interrupted, substituted, or interrupted and substituted by one or more groups each independently selected from the group consisting of aryl, heteroaryl, O, S, SO, $SO_2$, CO, COO, halogen, cyano, ester, ether, keto, hydroxy, alkoxy, aryloxy, amino, amido, $—[O(Si(R^{10})_2]_n—$, and $R^{10}[Si(R^{10})_2]_n—$; a $C_6$ to $C_{24}$ aryl; a $C_6$ to $C_{24}$ aryl substituted by one or more groups each independently selected from the group consisting of aryl, heteroaryl, O, S, SO, $SO_2$, CO, COO, halogen, cyano, ester, ether, keto, hydroxy, alkoxy, aryloxy, amino, amido, and $R^{10}[Si(R^{10})_2]_n$—; a $C_4$ to $C_{24}$ heteroaryl; a $C_4$ to $C_{24}$ heteroaryl substituted by one or more groups each independently selected from the group consisting of halogen, cyano, ester, ether, keto, hydroxy, alkoxy, aryloxy, amino, amido, and $R^{10}[Si(R^{10})_2]_n$—; $R^{10}[Si(R^{10})_2]_n$—; and $R^{11}$ which is a silicone residue derived from a silicone represented by the formula $R^{11}OH$ having a molecular weight up to about 30,000;

each $R^1$, $R^2$, $R^3$, $R^4$, $R^5$, $R^7$, $R^8$ and $R^9$ is independently selected from the group consisting of hydrogen, halogen, cyano, ester, ether, keto, hydroxy, alkoxy, aryloxy, amino, amido, a linear, branched or cyclic alkyl of 1–12 carbon atoms, a substituted linear, branched or cyclic alkyl of 1–12 carbon atoms, an aryl of 5–12 carbon atoms, a substituted aryl of 5–12 carbon atoms, a heteroaryl of 4–12 carbon atoms, and a substituted heteroaryl of 4–12 carbon atoms; wherein each substituent in the substituted alkyl, substituted aryl and substituted heteroaryl groups is independently selected from the group consisting of aryl, heteroaryl, halogen, cyano, ester, ether, keto, hydroxy, alkoxy, aryloxy, amino, and amido;

each $R^6$ is independently selected from the group consisting of hydrogen, an alkyl of 1–12 carbon atoms, and a substituted alkyl of 1–12 carbon atoms;

each $R^{10}$ is independently selected from the group consisting of alkyl, alkoxy, aryl and aryloxy; and n is from 1 to about 500.

2. The sunscreen of claim 1, wherein the $R^{11}OH$ is selected from the group consisting of a substituted or unsubstituted siloxane, and a substituted or unsubstituted organosiloxane.

3. The sunscreen of claim 1, wherein each R is independently selected from the group consisting of a linear, branched and cyclic $C_{18}$ to $C_{50}$ alkyls.

4. The sunscreen of claim 3, wherein R is selected from the group consisting of a linear, branched and cyclic $C_{18}$ to $C_{40}$ alkyls.

5. The sunscreen of claim 4, wherein R is selected from the group consisting of a linear, branched and cyclic $C_{20}$ to $C_{50}$ alkyls.

6. The sunscreen of claim 5, wherein R is selected from the group consisting of a linear, branched and cyclic $C_{20}$ to $C_{40}$ alkyls.

7. The sunscreen of claim 6, wherein R is selected from the group consisting of a linear, branched and cyclic $C_{22}$ to $C_{50}$ alkyls.

8. The sunscreen of claim 7, wherein R is selected from the group consisting of a linear, branched and cyclic $C_{22}$ to $C_{40}$ alkyls.

9. The sunscreen of claim 1, wherein R is selected from the group consisting of linear $C_{16}$ to $C_{50}$ alkyl; a linear $C_{16}$ to $C_{50}$ alkyl interrupted or substituted by one or more groups each independently selected from the group consisting of O, S, $SO_2$, COO, halogen, ester, alkoxy, hydroxy, —[O(Si$(R^{10})_2]_n$—, and $R^{10}[Si(R^{10})_2]_n$—.

10. The sunscreen of claim 1, wherein $R^{11}$ is $R^{10}[Si(R^{10})_2]_n$—.

11. The sunscreen of claim 1, wherein the molecular weight of the $R^{11}OH$ is about 100 to about 5,000.

12. The sunscreen of claim 1, wherein each $R^1$, $R^2$, $R^3$, $R^4$, $R^5$, $R^7$, $R^8$ and $R^9$ is hydrogen.

13. The sunscreen of claim 1, wherein each $R^6$ is independently selected from the group consisting of hydrogen and an alkyl.

14. The sunscreen of claim 1, wherein $R^{10}$ is alkoxy.

15. The sunscreen of claim 1, wherein n is from 1 to about 100.

16. A cosmetic composition comprising:
a cosmetically acceptable vehicle; and
an effective amount of a sunscreen selected from the group consisting of compounds represented by the formula:

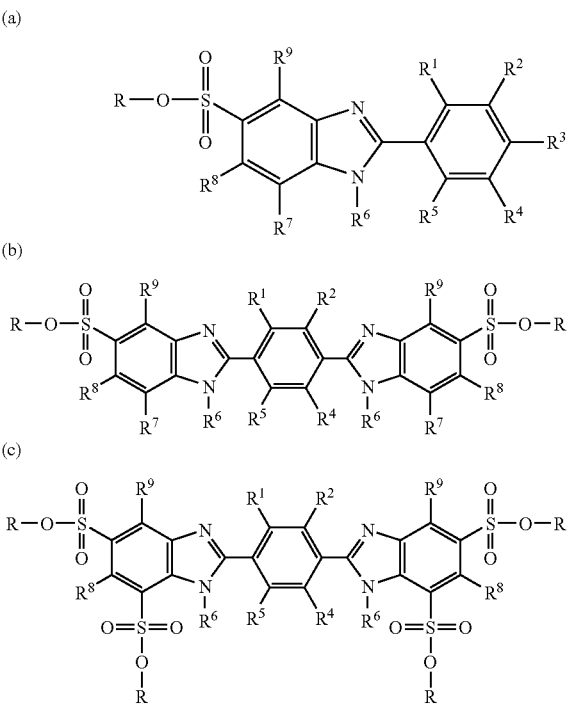

and
(d) any mixtures thereof;
wherein each R is independently selected from the group consisting of a linear, branched or cyclic $C_{16}$ to $C_{50}$ alkyl; a linear, branched or cyclic $C_{16}$ to $C_{50}$ alkyl interrupted, substituted, or interrupted and substituted by one or more groups each independently selected from the group consisting of aryl, heteroaryl, O, S, SO, $SO_2$, CO, COO, halogen, cyano, ester, ether, keto, hydroxy, alkoxy, aryloxy, amino, amido, —[O(Si$(R^{10})_2]_n$—, and $R^{10}[Si(R^{10})_2]_n$—; a $C_6$ to $C_{24}$ aryl; a $C_6$ to $C_{24}$ aryl substituted by one or more groups each independently selected from the group consisting of aryl, heteroaryl, O, S, SO, $SO_2$, CO, COO, halogen, cyano, ester, ether, keto, hydroxy, alkoxy, aryloxy, amino, amido, and $R^{10}[Si(R^{10})_2]_n$—; a $C_4$ to $C_{24}$ heteroaryl; a $C_4$ to $C_{24}$ heteroaryl substituted by one or more groups each independently selected from the group consisting of halogen, cyano, ester, ether, keto, hydroxy, alkoxy, aryloxy, amino, amido, and $R^{10}[Si(R^{10})_2]_n$—; $R^{10}[Si(R^{10})_2]_n$—; and $R^{11}$ which is a silicone residue derived from a silicone represented by the formula $R^{11}OH$ having a molecular weight up to about 30,000;

each $R^1$, $R^2$, $R^3$, $R^4$, $R^5$, $R^7$, $R^8$ and $R^9$ is independently selected from the group consisting of hydrogen, halogen, cyano, ester, ether, keto, hydroxy, alkoxy, aryloxy, amino, amido, a linear, branched or cyclic alkyl of 1–12 carbon atoms, a substituted linear, branched or cyclic alkyl of 1–12 carbon atoms, an aryl of 5–12 carbon atoms, a substituted aryl of 5–12 carbon atoms, a heteroaryl of 4–12 carbon atoms, and a substituted heteroaryl of 4–12 carbon atoms; wherein each substituent in the substituted alkyl, substituted aryl and substituted heteroaryl groups is independently selected from the group consisting of aryl, heteroaryl, halogen, cyano, ester, ether, keto, hydroxy, alkoxy, aryloxy, amino, and amido;

each $R^6$ is independently selected from the group consisting of hydrogen, an alkyl of 1–12 carbon atoms, and a substituted alkyl of 1–12 carbon atoms;

each $R^{10}$ is independently selected from the group consisting of alkyl, alkoxy, aryl and aryloxy; and n is from 1 to about 500.

17. The cosmetic composition of claim 16, further comprising a cosmetically active ingredient selected from the group consisting of one or more insect repellents, jelly fish repellents, poison ivy protective agents, poison oak protective agents, poison sumac protective agents, anesthetics, anti-allergenics, antifungals, antimicrobials, anti-inflammatory agents, antiseptics, exfollients, pharmaceuticals, film formers, additional sunscreens, and any combinations thereof.

18. The cosmetic composition of claim 16, wherein the additional sunscreen is selected from the group consisting of dibenzoylmethane, oxybenzone, sulisobenzone, dioxybenzone, menthyl anthranilate, para aminobenzoic acid ester, benzophone-3, butyldibenzoylmethane, dimethyl cinnamate, octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, 3-benzylidene camphor, benzylidene camphor sulfonic acid ester, octyl triazone, phenyl benzimidazole sulfonic acid ester, terephthalydiene dicamphor sulfonic acid ester, di-t-butyl hydroxybenzylidene camphor, ethyl PABA, butylmethoxy dibenzoylmethane, terephthalydiene methylene bis-benzotriazoyltetramethylbutyl-phenol, diethylhexyl-2,6-naphthalate, bis-ethylhexyloxyphenol methoxyphenol triazine, hydroxy methylphenyl benzotriazole, methylene bis-benzotriazoyltetramethylbutylphenol, bis-ethylhexyloxyphenol methoxyphenol triazine, hydroxybenzophenone, a benzotriazole, a dibenzoyl methane, an oxanilide, a hydroxy cinnamate, oil dispersible titanium dioxide, oil dispersible zinc oxide, a silicone-anchored sunscreen, para aminobenzoic acid, salicylic acid, TEA salicylate, benzylidene camphor sulfonic acid, phenyl benzimidazole sulfonic acid, terephthalydiene dicamphor sulfonic acid, hydroxy cinnamic acid, any derivatives thereof, and any combinations thereof.

19. The cosmetic composition of claim 16, wherein the sunscreen is present up to about 50 wt % based on the total weight of the cosmetic composition.

20. The cosmetic composition of claim 19, wherein the sunscreen is present at about 1.0 wt % to about 40 wt % based on the total weight of the cosmetic composition.

21. The cosmetic composition of claim 20, wherein the sunscreen is present at about 10 wt % to about 35 wt % based on the total weight of the cosmetic composition.

22. The cosmetic composition of claim 16, wherein the cosmetic composition exhibits an SPF about 15 to about 75.

23. The cosmetic composition of claim 22, wherein the cosmetic composition exhibits an SPF about 25 to about 65.

24. The cosmetic composition of claim 23, wherein the cosmetic composition exhibits an SPF about 30 to about 50.

25. The cosmetic composition of claim 16, wherein the cosmetic composition is a product selected from the group consisting of shampoo, hair conditioner, styling mousse, hair treatment preparation, hair coloring product, semi-perm product, oxidation dye, body wash, bar soap, liquid soap, skin care preparation, lipstick, mascara, color cosmetic, nail care preparation, and any combinations thereof.

26. The cosmetic composition of claim 25, wherein the cosmetic composition is a product form selected from the group consisting of foam, mousse, solution, emulsion, cream, lotion, pomade, balm, stick, gel, pump spray, and aerosol spray, and any combinations thereof.

27. A method of protecting skin from exposure to the sun, comprising:
applying topically to the skin an effective amount of a cosmetic composition according to claim 16.

28. A method of protecting skin from exposure to the sun and simultaneously repelling insects from the skin, the method comprising:
topically applying to the skin an effective amount of a cosmetic composition according to claim 16, which cosmetic composition further comprises an insect repellant.

29. The cosmetic composition of claim 28, wherein the mixture of the sunscreen and insect repellent is up to about 70 wt % based on the total weight of the cosmetic composition.

* * * * *